US005652221A

United States Patent [19]
Larner et al.

[11] Patent Number: 5,652,221
[45] Date of Patent: Jul. 29, 1997

[54] METHOD OF TREATING DEFECTIVE GLUCOSE METABOLISM USING SYNTHETIC INSULIN SUBSTANCES

[75] Inventors: Joseph Larner; John Price, both of Charlottesville; Thomas Picariello, Blacksburg; Laura Huang, Charlottesville, all of Va.

[73] Assignee: The University of Virginia Patent Foundation, Christiansburg, Va.

[21] Appl. No.: 335,015

[22] Filed: Nov. 7, 1994

[51] Int. Cl.$^6$ .......................... A61K 31/70; C07H 15/207
[52] U.S. Cl. .............................. 514/35; 536/17.2; 514/25; 514/62; 514/866
[58] Field of Search .......................... 536/17.2; 514/25, 514/35, 866, 62

[56] References Cited

U.S. PATENT DOCUMENTS

| | | | |
|---|---|---|---|
| 4,446,064 | 5/1984 | Larner et al. | 530/344 |
| 4,839,466 | 6/1989 | Saltiel | 530/395 |
| 4,906,468 | 3/1990 | Saltiel | 424/172.1 |
| 5,124,360 | 6/1992 | Larner et al. | 514/738 |

FOREIGN PATENT DOCUMENTS 0245956  11/1987  European Pat. Off. .

OTHER PUBLICATIONS

Ellestad et al. *J. Antibiotics* 1982, 35(10), 1418–1421.
Mohlenkamp et al. *Aminoglycoside Antibiotics* 1968, 33(8), 3163–3165.
Larner et al. *Biochem. Biophys. Res. Commun.* 1988, 151(3), 1416–1426.
Machicao et al. *Biochem. J.* 1990, 266, 909–916.
Berlin et al. *Tetrahedron* 1991, 47(1), 1–20.
Berlin et al., *Synthesis of Hexosamine–Inositol–Phosphates Related to Putative Insulin Mediators,* vol. 47, No. 1, pp. 1–20, 1991.
Berlin et al, *Synthesis of 2–Amino–2–Deoxy–D–Galactosyl–a–1, 3–D–Chiro–Inositol,* Tetrahedron Ltrs., vol. 31, No. 8, pp. 1109–1112, 1990.
Plourde et al., *Synthesis of a Potentially Insulin–Mimetic Phosphodisaccharide,* Tetrahedron Ltrs., vol. 31, No. 19, pp. 2693–2696, 1990.

Plourde et al., *Synthesis and Characterization of an Insulin–Mimetic Disaccharide,* J. Org. Chem., vol. 57, No. 9, pp. 2606–2610, 1992.
Larner et al., *Generation by Insulin of a Chemical Mediator that Controls Protein Phosphorylation/Dephosphorylation,* Science, vol. 206, pp. 1408–1410, 1979.
Saltiel et al., *In Search of a Second Messenger for Insulin,* Invited Review, pp. C1–C11, 1988 Copyright the American Physiological Society.
Saltiel et al., *Functional Consequences of Lipid–Mediated Protein–Membrane Interactions,* Biochemical Pharmacology, vol. 42, No. 1, pp. 1–11, 1991.
Saltiel, *Transmembrane Signaling in Insulin Action,* Insulin Action, pp. 107–116, 1989 Alan R. Liss, Inc.
Saltiel, *The Role of Glycosyl–Phosphoinositides in Hormone Action* Journal of Bioenergetics and Biomembranes, vol. 23, No. 1, pp. 29–41, 1991.
Saltiel, *Second Messengers of Insulin Action,* TEM Jan./Feb., pp. 158–163 1990.
Saltiel, *Signal Transduction in Insulin Action,* J. Nutr. Biochem, vol. 1, pp. 180–189, Apr. 1990.
Falck et al., *Total Synthesis of the 5–Methylenephosphonate Analogue of d–myo–Inositol 1,4,5–Triphosphate,* J. Chem. Soc. Chem. Commun., 953–955, 1990.
Falck et al., *Enantiospecific Synthesis of d–myo–Inositol 1,4,5–Trisphosphate from (–) Quinic Acid,* Journ. of Organic Chemistry, vol. 54, pp. 5851–5852, 1989.
Falck et al., *Total Synthesis of d–myo–Inositol 3,4,5–Trisphosphate and 1,3,4,5–Tetrakisphosphate,* Biorg. & Med. Chem Ltrs, vol. 3, No. 4, pp. 717–720, 1993.
Falck et al., *Enantiospecific Synthesis of Inositol Polyphosphates, Phosphatidylinositides & Analogues from (–)–Quinic Acid,* Reprint ACS Symps, pp. 145–154, 1991.

Primary Examiner—Gary L. Kunz
Assistant Examiner—Kathleen Kahler Fonda
Attorney, Agent, or Firm—Sterne, Kessler, Goldstein & Fox P.L.L.C.

[57] ABSTRACT

A synthetic insulin mimetic compound is disclosed. Small synthetic amines of disaccharides, such as 2-deoxy-2-amino-galactopyranosyl pinitol are shown to mimic the action of insulin and to modulate its action.

17 Claims, 7 Drawing Sheets

FIG. 2 SCHEME 1

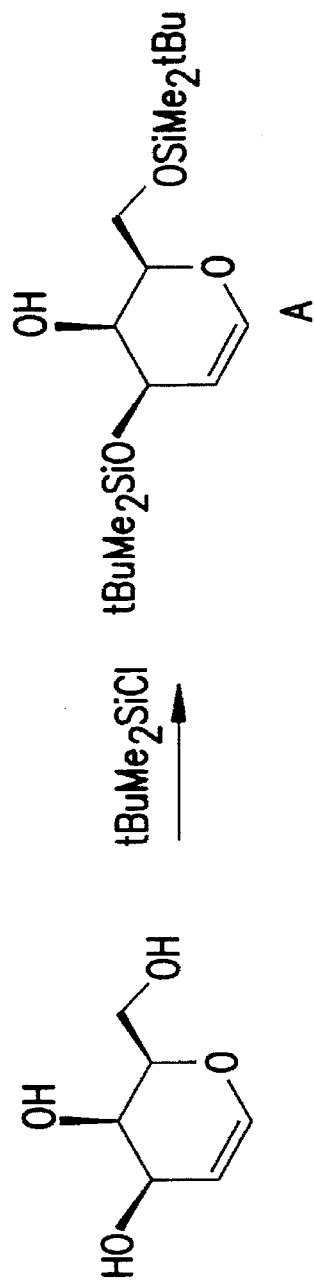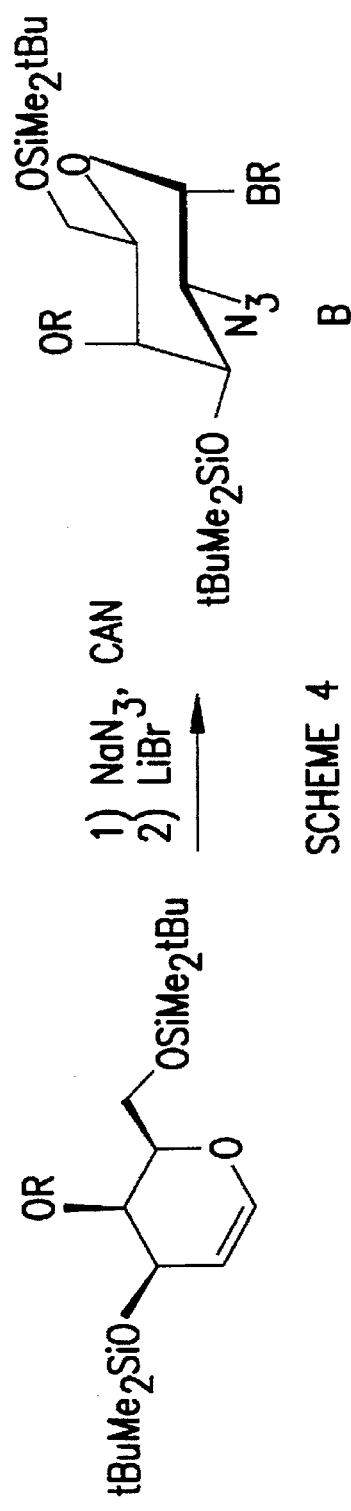
FIG. 4

FIG.5 SCHEME 5

FIG.6 SCHEME 6

SCHEME 7

METHOD OF TREATING DEFECTIVE GLUCOSE METABOLISM USING SYNTHETIC INSULIN SUBSTANCES

This invention was made with government support under Grant 5-R37-DK-14334-21 awarded by the National Institutes of Health. The government has certain rights in the invention.

BACKGROUND OF THE INVENTION

This invention relates to substances which mimic the action of insulin.

It has long been known that the cellular metabolic actions of Insulin involve the generation of a low molecular weight substance that mimics certain actions of insulin. See, U.S. Pat. No. 4,446,064. An inositol glycan structure was first proposed for an insulin mediator in 1986. See, Saltiel, A. R. et al. Proc. Nat. Acad. Sci. Vol. 83, pp 5793–97 (1986). Since these initial studies, structural variations in the insulin mediator have been reported in a number of laboratories. See, Saltiel, *Second Messengers of Insulin Action*, Diabetes Care, Vol. 13, No. 3, pp.244–256 (1990). Specifically, compositional analyses from the laboratory of Larner demonstrated the presence of significant amounts of D-chiroinositol and galactosamine as features of the inositol glycan structure. Larner et al., Biochem. Biophys. Res. Comm. Vol. 151, pp.1416–26 (1988). Despite progress in identifying the structure and biogenesis of inositol glycans released from the plasma membrane in response to insulin, identification of the precise biological utility of these compounds will depend upon the precise structural identification and examination of their insulin mimetic properties.

The identification of substances that mediate or mimic the action of insulin could lead to the development of novel structures which may be of clinical use in the treatment of persons having disorders of glucose metabolism, such as impaired glucose tolerance, elevated blood glucose associated with Type II diabetes, and insulin resistance.

Insulin mimetic molecules extracted from biological sources present a variety of undesirable characteristics, including possible contamination as well as unreliable or limited sources of supply of naturally occurring molecules. It is, therefore, desirable to devise a synthetic molecule which mimics the activity of insulin or its mediators and which can be synthesized without resort to extracts from animal tissue.

SUMMARY OF THE INVENTION

It has been found that certain small amino disaccharides can mimic the action of insulin. Specifically, they act to reduce elevated blood glucose levels. These substances consist of an amino sugar moiety and inositol, joined by a beta linkage. Derivatives of these disaccharides also act to reduce elevated blood glucose levels. Examples of amino sugars used in the present invention include glucosamine and galactosamine. The 2-deoxy form of these compounds is most preferred (e.g., 2-deoxy-2-amino hexapyranosyl inositols). Amino disaccharides of the present invention include molecules consisting of amino derivatives of galactopyranose and isomers and derivatives of inositol. Compounds such as 2-deoxy-2-amino-galactopyranosyl pinitol are most important in this regard. It has also been found that beta anomers are most important.

Examples of substances within the scope of this invention include various derivatives of these amino disaccharides, such as 4'-O-(2 deoxy-2-amine-D-galactopyranosyl)-D-pinitol-5'-phosphate or 4'-O-(2 deoxy-2-amine-D-galactopyranosyl)-D-pinitol-2'-phosphate.

DESCRIPTION OF THE FIGURES

FIGS. 2 through 7 illustrate synthetic pathways used to prepare compounds of the present invention.

DETAILED DESCRIPTION OF THE INVENTION

Figure 1:
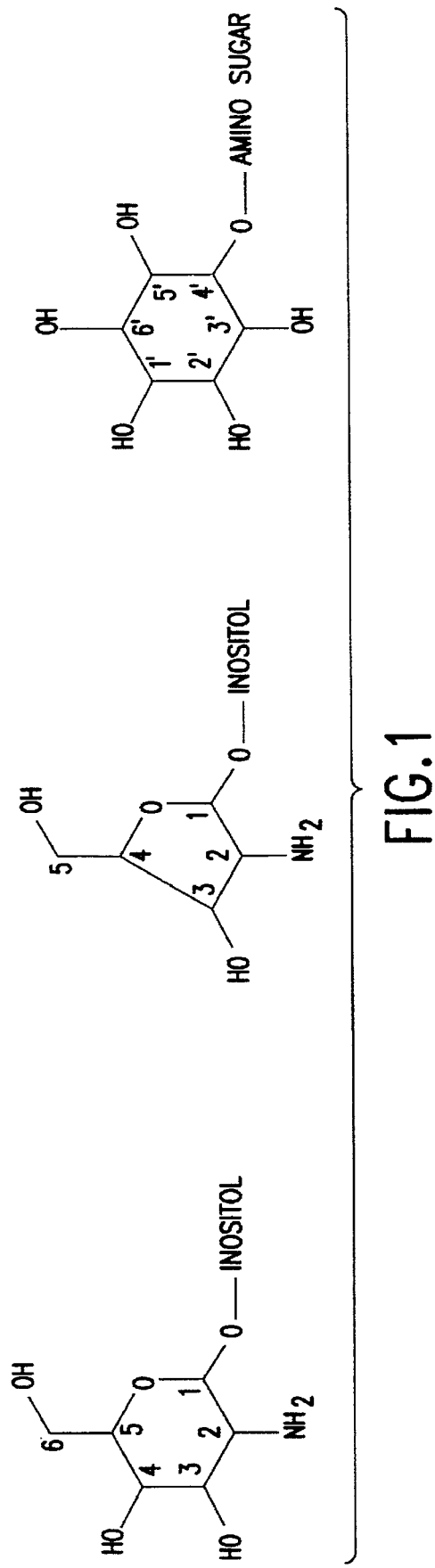
FIG. 1 is an illustration of the numbering system used to describe compounds of the present invention.

The present invention contemplates a broad range of compounds. The amino sugar component of these compounds is preferably a hexosamine or a pentose amine, with hexose amines, such as allosamine and gulosamine generally preferred, especially glucosamine, and galactosamine. Among the inositols, chiroinositol and myoinositol are preferred. The numbering system used to describe the compounds of the present invention is shown in FIG. 1.

The hydroxyl groups of both the amino sugar and the inositol component may be replaced by a variety of substituents. Alkoxy, aryloxy, ether, ester, and phosphate group replacements are useful in protecting the molecule, modifying its hydrophilicity or modulating its insulin-mimetic properties. Replacement of the hydroxyl group at the number 3 position of chiroinositol is preferred, with replacement with a methoxy group (i.e. pinitol) especially preferred. Substitutions at the 2 and 1 positions of chiroinositol (as well as at the corresponding positions of other inositol components) are also preferred.

Insulin mimetics of this invention can be prepared in the following manner.

Figure 2:
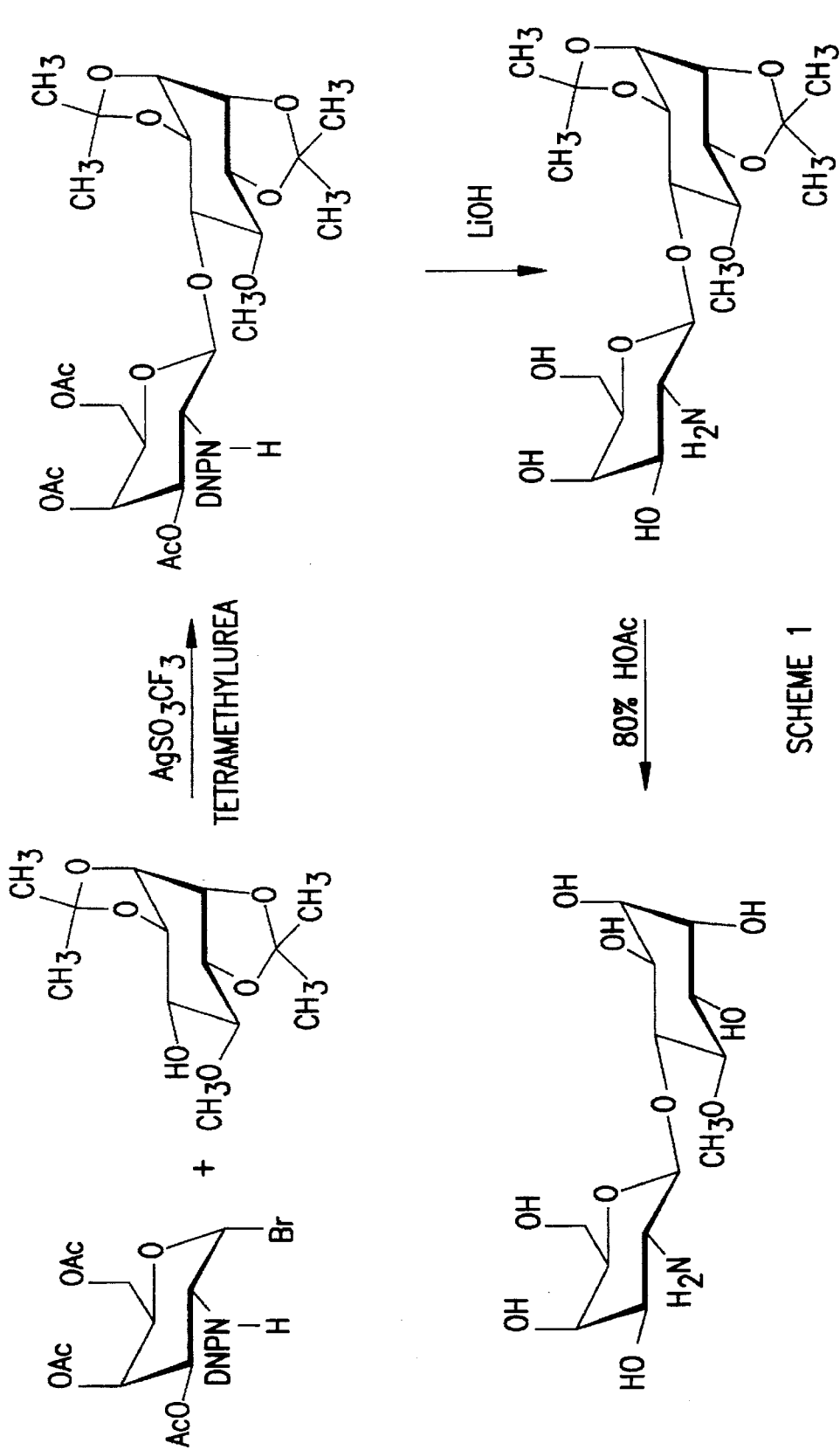

The beta-glycosides of 2-deoxy-2-amino sugars with derivatives of inositol of this invention are prepared by the reaction of an appropriately protected amino sugar precursor having a leaving group at the 1-position (glycosyl donor) with a free hydroxyl group of a suitably protected inositol (glycosyl acceptor) in the presence of a promoter, followed by deprotection. For example, 4'-O-(2-deoxy-2-amino-b-D-galactopyranosyl)-D-pinitol is prepared by the glycosylation/deprotection sequence shown in Scheme 1, which is set forth in FIG. 2.

Figure 3:
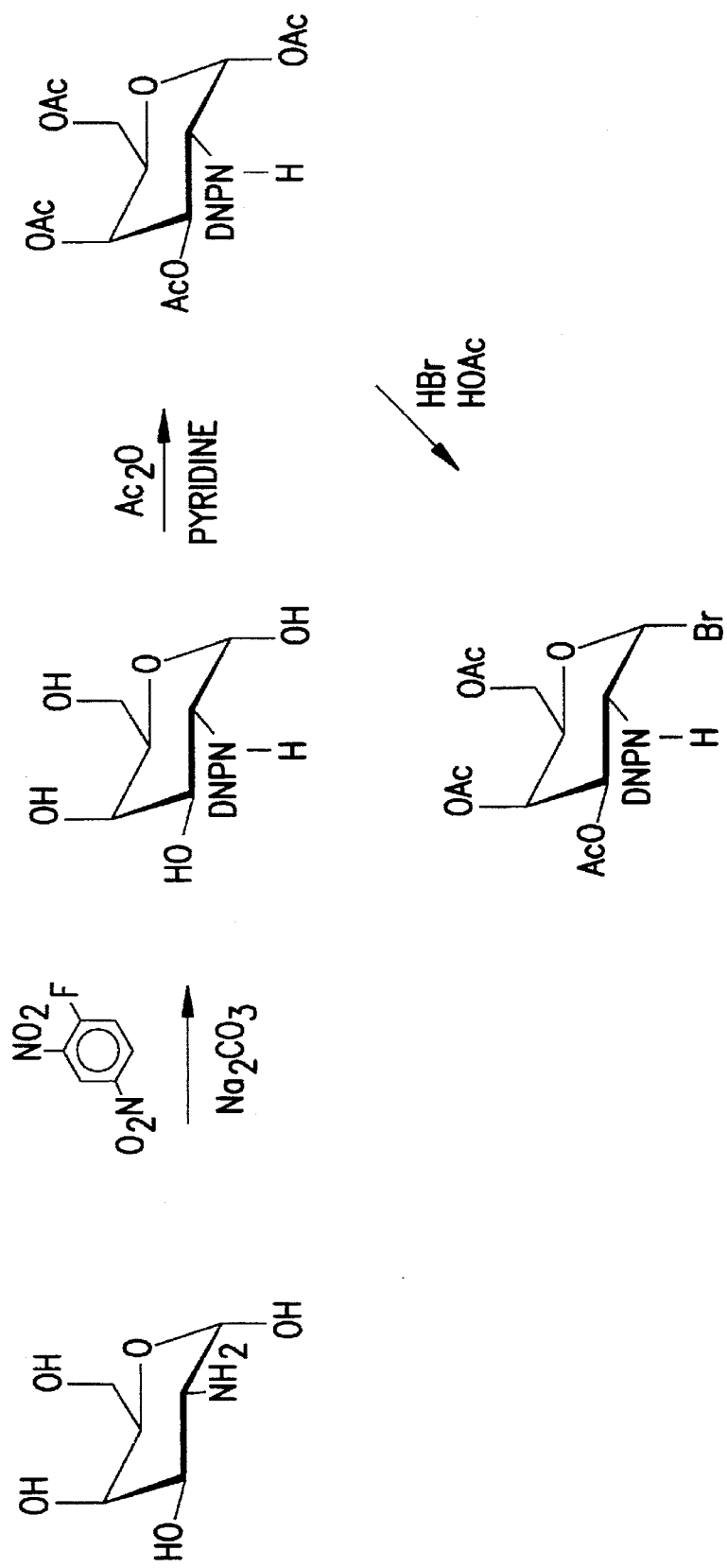

The glycosyl donor, 1-bromo-1,2-dideoxy-3,4,6-tri-O-acetyl-2-dinitrophenylaminogalactose, is prepared as shown in Scheme 2, which is set forth in FIG. 3, and described in detail below.

Other glycosyl donors are prepared by straight forward synthetic manipulation of available precursors. For instance, selective derivatization of the 4-position of galactal can be achieved by treating the compound with 2-equivalents of t-butyldimethylsilyl chloride as shown in Scheme 3, which is set forth in FIG. 4. Compound A can be easily converted to an ether or ester by known Williamson or Schotten-Bauman techniques. Azidonitration and bromide displacement on B provides a glycosyl donor which, following reaction with a glycosyl acceptor in the presence of silver silicate, reduction of the azido group by hydrogenation and deprotection with fluoride, yields a beta-glycoside of 2-deoxy-2-aminogalactose substituted at the 4-position with an ether or an ester.

Figure 5:
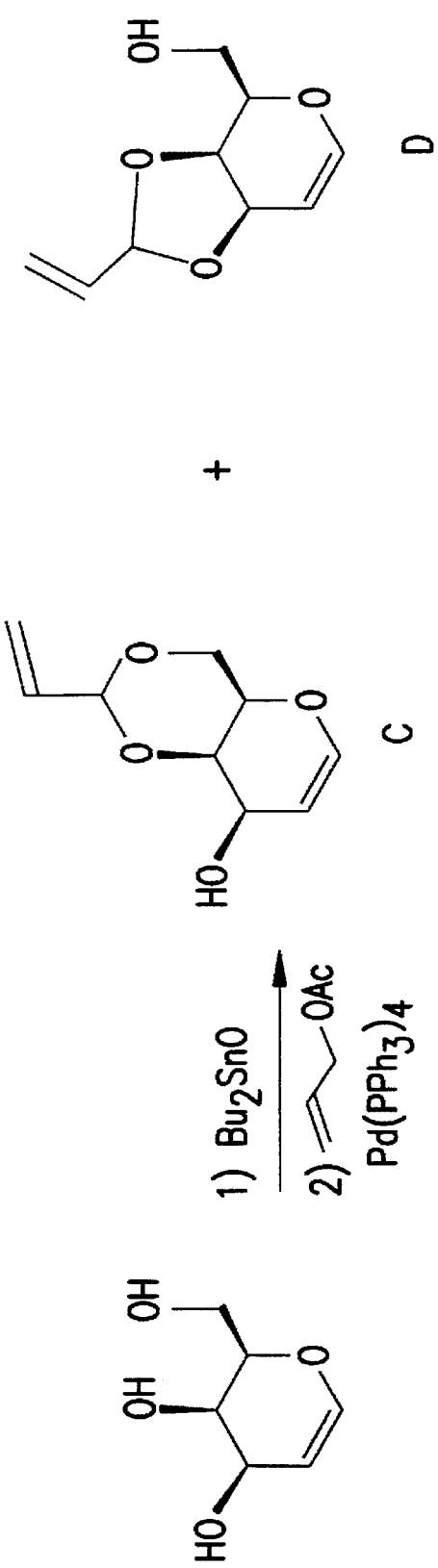

Similarly, as is shown in scheme 5 which is set forth in FIG. 5, compounds C and D can be easily separated and converted into beta-glycosides of 2-deoxy-2-aminogalactose substituted at the 3 or 6-position with an ether or an ester.

Figure 6:
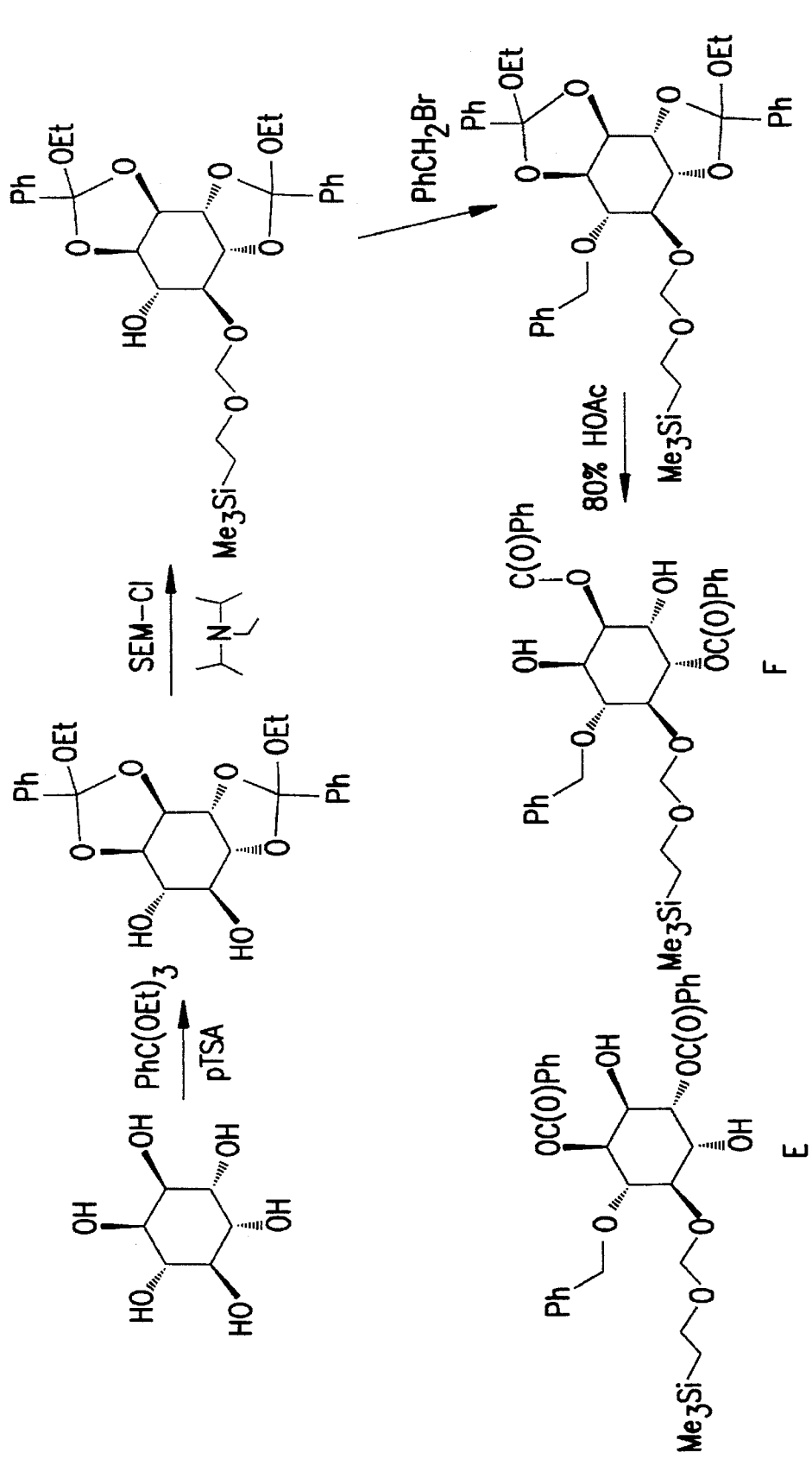
Figure 7:
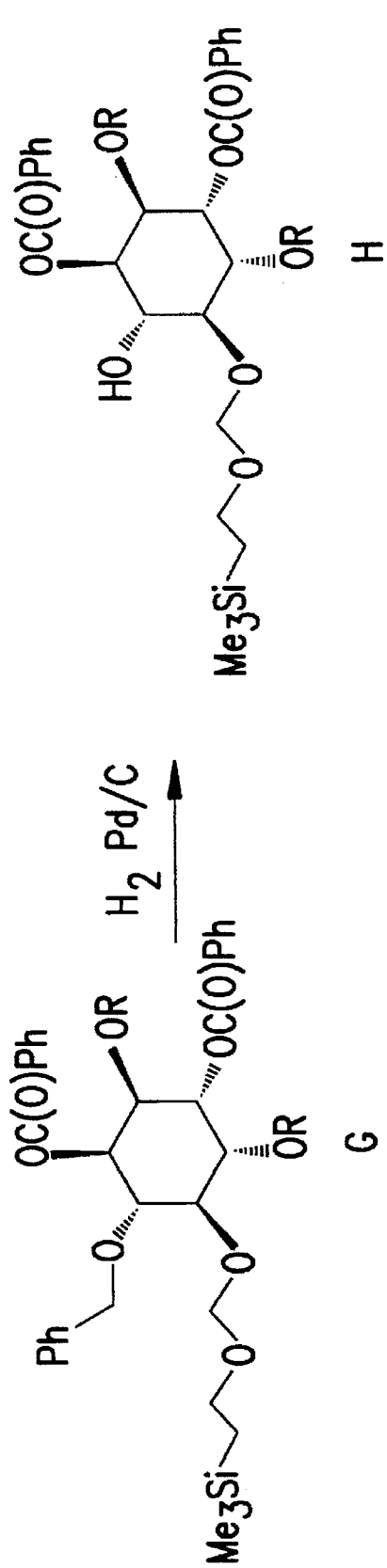

The glycosyl acceptor, 1',2';5',6'-di-O-isopropylidene-D-pinitol, used in the synthesis of 4'-O-(2-deoxy-2-amino-beta-D-galacopyranosyl)-D-pinitol as in Scheme 1 was prepared by the reaction of D-pinitol with dimethoxypropane in the presence of a catalytic amount of p-toluenesulfonic acid. Other glycosyl acceptors can be prepared readily. For instance, compounds E and F, which can be prepared as shown in Scheme 6, which is set forth in FIG. 6, can be mono or dialkylated regioselectivly using Williamson techniques. Glycosides containing chiroinositols with alkoxy substituents at the 2 and 6 positions can be obtained by catalytic debenzylation of G to give glycosyl acceptor H as set forth in FIG. 7, followed by glycosylation of H and deprotection using standard techniques. Similarly, glycosides containing chiroinositols with alkoxy substituents at the 1 and 5-positions can be prepared from G.

I. Preparation of 4'-O-(2-deoxy-2-amino-beta-D-galactopyranosyl)-D-chiroinositol.

A detailed procedure for preparing this compound is as follows.

1. Preparation of 1',2';5',6'-di-O-isopropylidene-3-O-(trimethylsilylethoxymethyl)-D-chiroinositol.

1,2;5,6-Di-O-isopropylidene-D-chiroinositol (942 mg), 0.83 ml of trimethylsilylethoxymethyl chloride (SEM-Cl) and 1.9 ml of diisopropylethyl amine (DIPEA) were dissolved in 20 ml of dry methylene chloride and refluxed for 16 hours. The solution was concentrated in vacuo and the last traces of volatile material were removed under high vacuum (500 m Torr) for four days to yield pure product. The yield was 1.04 g (73%).

2. Preparation of 2-deoxy-2-dinitrophenylamino D-galactose.

Galactosamine hydrochloride (10 g) was stirred with 20 ml of distilled acetone and 50 ml of deionized water. 2,4-Dinitrofluorobenzene (5.8 ml) was added followed by 4.9 g of sodium carbonate. The mixture was stirred at room temperature for 18 hours when a yellow precipitate was formed. The material was suction filtered to dryness, dissolved in 30 ml of dry methanol. Benzene (120 ml) was added followed by enough hexane to make the solution slightly cloudy (approximately 50 ml) at which time the cloudy suspension was seeded to produce 5.6 g (35%) of the product.

An alternate procedure was used to concentrate the mixture after 18 hours reaction time and load the crude material on a 3×20 cm flash column packed with silica gel 60 and elute the column with 3:1 chloroform:isopropanol and removing the solvent in vacuo to dryness. From 6 g of galactosamine hydrochloride, 3.48 ml of dinitrofluorobenzene, 2.94 g of sodium carbonate, 30 ml of water and 120 ml of acetone, 7.37 g (77%) of the product was obtained.

Preparation of 1,3,4,6-tetra-O-acetyl-2-deoxy-2-dinitrophenylamino-D-galactose.

2-Deoxy-2-dinitrophenylamino galactose (7.37 g) was dissolved in 50 ml of dry pyridine and the solution was cooled to 0° C. Acetic anhydride (50 ml) was added and the solution stirred for ten hours while allowing to warm to 10°–15° C. The solution was poured into 500 ml of ice water and the mixture was suction filtered. The precipitate was recrystallized from 500 ml hot 95% ethanol to yield 11.06 g (100%) of the product.

3. Preparation of 1-bromo-1,2-dideoxy-2-dinitrophenylamino-3,4,6-tri-O-acetyl-D-galactose.

1,3,4,6-Tetra-O-acetyl-2-deoxy-2-dinitrophenylamino-galactose (6.83 g) was moistened with 12 ml of dry chloroform and cooled to 0° C where 100 ml of 30% hydrogen bromide in acetic acid was added dropwise and the solution was stirred for two hours after the addition was complete. The solution was poured into 350 ml of ice water and extracted with 4×100 ml of chloroform. The combined chloroform extracts were washed with 2×100 ml saturated aqueous sodium bicarbonate, 100 ml of water, dried over magnesium sulfate, filtered and concentrated in vacuo. After 25 hours of drying under high vacuum, 7.08 g (99%) of the product was obtained.

1. Glycosylation procedure to prepare 4'-O-[3,4,6-tri-O-acetyl-2-deoxy-2-dinitrophenylamino-,β-D-galactopyranosyl]-3'-O-trimethylsilylethoxymethyl-1',2';5',6'-di-O-isopropylidene-D-chiroinositol.

Vacuum dried 1-bromo-1,2-dideoxy-3,4,6-tri-O-acetyl-2-dinitrophenylamino-D-galactose (170 mg) and 1,2;5,6-di-O-isopropylidene-3-O-(trimethylsilylethoxymethyl)-D-chiroinositol (100 mg) were dissolved in 10 ml of dry methylene chloride and the solution stirred at room temperature. Under a nitrogen shroud, 500 mg of freshly activated 4 angstrom powdered molecular sieves was added and stirred for one hour. At that time 0.04 ml of tetramethyl urea and 82 mg of silver triflate were added under a nitrogen shroud. The heterogeneous mixture was stirred at room temperature for 21 hours where three drops of triethylamine was added; the mixture was filtered and the solvents removed in vacuo. The crude material was loaded on a 2×25 cm flash column packed with silica gel 60 and the column was eluted with 790 ml of 4:1 petroleum ether:ethyl acetate and 100 ml of 2:1 petroleum ether:ethyl acetate to isolate 90 mg of the—isomer (23%) and 42 mg of the beta-isomer (19%)

1. Preparation of 4'-O-[2-deoxy-2-amino-beta-D-galactopyranosyl]-3'-O-trimethylsilylethoxymethyl-1',2';5',6'-di-O-isopropylidene-D-chiroinositol.

4'-O-[3,4,6-Tri-O-acetyl-2-deoxy-2-dinitrophenylamino-beta-D-galactopyranosyl]-3'-O-trimethylsilylethoxymethyl-1',2';5',6'-di-O-isopropylidene-D-chiroinositol (37.5mg) was stirred with 3.5 ml of 1M aqueous lithium hydroxide and 7 ml of dioxan and heated to 90° C. for 28 hours. Acetic acid (4 ml) was added to pH 5 and the solvents were removed in vacuo. The residue was dissolved in methanol, 1 g of silica gel 60 was added and the methanol was removed in vacuo. The preabsorbed material was loaded on a 1×15 cm flash column packed with silica gel 60 and the column was eluted with 3:1 chloroform:isopropanol to isolate 22.1 mg of the product (90%).

2. Preparation of 4'-O-[2-deoxy-2-amino-beta-D-galactopyranosyl]-D-chiroinositol.

4'-O-[2-Deoxy-2-amino-beta-D-galactopyranosyl]-3'-O-trimethylsilylethoxymethyl-1',2';5',6'-di-O-isopropylidene-D-chiroinositol (124 mg) was dissolved in 10 ml of 80% acetic acid and the solution heated to 75° C. for 18 hours. The solvents were removed in vacuo to yield 76 mg (99%) of the product. The product was further purified using HPLC with a $C_{18}$ stationary phase and a water eluant.

1. Preparation of 4'-O-(2-deoxy-2-amino-beta-D-galactopyranosyl)-D-pinitol.

A detailed description of the synthetic pathway by which this compound is prepared is as follows.

2. Preparation of 4'-O-[2-deoxy-2-dinitrophenylamino-3,4,6-tri-O-acetyl-beta-galactopyranosyl]-1',2';5',6'-di-O-isopropylidene-D-pinitol.

Vacuum dried 1-bromo-1,2-dideoxy-3,4,6-tri-O-acetyl-2-dinitrophenylamino-galactose (3.9 g) and 1 g of 1,2;5,6-di-O isopropylidene-D-pinitol were dissolved in 100 ml of dry methylene chloride and the solution stirred at room temperature. Under a nitrogen shroud, freshly activated 4 angstrom powdered molecular sieves was added and the mixture stirred for one hour. At that time 0.87 ml of tetramethyl urea and 1.86 of vacuum dried silver triflate was added under a nitrogen shroud and the mixture stirred at 0° C. for 18 hours. The mixture was filtered and the filtrate was dried in vacuo. The crude oil was loaded on a 5×20 cm flash column packed with silica gel 60 and the column was eluted with 2:1 petroleum ether:ethyl acetate to yield 2.108 g (76%) of the beta anomer.

3. Preparation of 4'-O-[2-deoxy-2-amino-beta-D-galactopyranosyl]-1',2';5',6'-di-O-isopropylidene-D-pinitol.

4'-O-[3,4,6-Tri-O-acetyl-2-deoxy-2-dinitrophenylamino-beta-D-galactopyranosyl]-1',2';5',6'-di-O-isopropylidene-D-pinitol (902.1 mg) was stirred with 3.5 ml of 1M aqueous lithium hydroxide and 7 ml dioxan and heated to 95° C. for 72 hours. Acetic acid (2 ml) was added and the solvents were removed in vacuo. The crude material was loaded on a 2×10 cm flash column packed with silica gel 60 and eluted with 3:1 chloroform:isopropanol to yield 361 mg (61%) of the product, which was recrystallized from isopropanol to yield 74 mg of crystalline product.

4. Preparation of 4'-O-(2-deoxy-2-amino-beta-D-galactopyranosyl)-D-pinitol.

4'-O-[2-Deoxy-2-amino-beta-D-galactopyranosyl]-1', 2';5',6'-di-O-isopropylidene-D-pinitol (101 mg) was dissolved in 5 ml of 80% acetic acid and the solution heated to 75° C. for 24 hours. The solvents were removed in vacuo. The residue was passed through a C-18 Millipore cartridge and eluted with acetonitrile. The residue (which weighed 64 mg) was recrystallized from isopropanol to yield 25 mg of the product.

Reduction of Elevated Blood Glucose Concentration

These compounds are useful in the treatment of defects in glucose metabolism such as impaired glucose tolerance insulin resistance, or the elevated blood sugar associated with type II diabetes. For example, rats were injected intravenously with 70 mg/kg of streptozotocin. After ten days, when resultant hyperglycemia was established, the animals were anesthetized with ketamine and zero time blood glucose levels were established by way of tail vein sampling. An experimental group was given 2 mg/kg 4'-O-(2-deoxy-2-amino-beta-D-galactopyranosyl)-D-pinitol by intravenous injection via the tail vein, and a control group was given an equal volume of saline. Blood glucose levels were measured over time in both groups. All measurements were made while the subjects were under ketamine anesthesia. Evaluation of the time course data by two-way analysis of variance indicated a significant overall effect of the disaccharide to lower blood glucose concentration ($p<0.01$). Thirty minutes after administration of the disaccharide, blood glucose levels were decreased from pretreatment concentration by 30% (±9.5) in the experimental group, while levels in the control group decreased only 2.5% (±2.6).

Compounds according to the present invention can be administered byway of a preparation containing a suitable carrier and an effective amount of the compound. Doses in the range of 0.1 to 10.0 mg/kg are preferred, with the range of 1.0 to 2.0 mg/kg most preferred.

What is claimed is:

1. A method for the treatment of defective glucose metabolism disorders selected from the group consisting of impaired glucose tolerance, elevated blood glucose associated with Type II diabetes, and insulin resistance, comprising administering to a person in need of such treatment an effective amount of a compound consisting of a 2-amino, D-hexosamine and an inositol, joined by a beta linkage.

2. The method of claim 1 wherein the inositol is selected from the group consisting of myo-inositol and chiro-inositol.

3. The method of claim 1 wherein the inositol is D-pinitol and the linkage to the hexosamine is 1,4'.

4. The method of claim 3 wherein the hexosamine is selected from the group consisting of D-glucosamine and D-galactosamine.

5. The method of claim 4 wherein the hexosamine is D-galactosamine.

6. The method of claim 2 or 5 wherein at least one of the hydroxyl groups is replaced by a substituent selected from the group consisting of phosphate, $C_1$–$C_6$ alkoxy, $C_3$–$C_6$ cycloalkoxy, $C_{3-6}$ ester, $C_6$ aryloxy, and $C_7$–$C_8$ arylalkoxy.

7. The method of claim 6 wherein at least one of the hydroxyl groups is replaced by a substituent selected from the group consisting of methoxy, ethoxy, and propoxy.

8. The method of claim 5 wherein a substituent selected from the group consisting of phosphate, $C_1$–$C_6$ alkoxy, $C_3$–$C_6$ cycloalkoxy, $C_{3-6}$ ester, $C_6$ aryloxy, and $C_7$–$C_8$ arylalkoxy replaces at least one of the hydroxyls at position 1', 2' or 6' of the inositol ring.

9. The method of claim 2 or 5 wherein at least one of the hydroxyl groups is replaced by a methoxy group or a phosphate group.

10. The method of claim 2 wherein the inositol is chiroinositol and the linkage to the hexosamine is 1,4'.

11. The method of claim 10 wherein the hexosamine is selected from the group consisting of D-glucosamine and D-galactosamine.

12. The method of claim 11 wherein the hexosamine is D-galactosamine.

13. The method of claim 2 or 12 wherein at least one of the hydroxyl groups is replaced by a substituent selected from the group consisting of phosphate, $C_1$–$C_6$ alkoxy, $C_3$–$C_6$ cycloalkoxy, $C_{3-6}$ ester, $C_6$ aryloxy, and $C_7$–$C_8$ arylalkoxy.

14. The method of claim 12 wherein at least one of the hydroxyl groups is replaced by a substituent selected from the group consisting of methoxy, ethoxy, and propoxy.

15. The method of claim 11 wherein a substituent selected from the group consisting of phosphate, $C_1$–$C_6$ alkoxy, $C_3$–$C_6$ cycloalkoxy, $C_{3-6}$ ester, $C_6$ aryloxy, and $C_7$–$C_8$ arylalkoxy replaces at least one of the hydroxyls at position 1', 2', 3' or 6' of the inositol ring.

16. The method of claim 2 or 11 wherein at least one of the hydroxyl groups is replaced by a substituent selected from the group consisting of a methoxy group, an amine, and a phosphate group.

17. 4'-O-(2-deoxy-2-amino-β-galactopyranosyl)-D-pinitol.

* * * * *